US009517342B2

(12) United States Patent
Costanzo et al.

(10) Patent No.: US 9,517,342 B2
(45) Date of Patent: Dec. 13, 2016

(54) OLFACTORY IMPLANT SYSTEM

(71) Applicant: VIRGINIA COMMONWEALTH UNIVERSITY, Richmond, VA (US)

(72) Inventors: Richard M. Costanzo, Crozier, VA (US); Daniel Coelho, Richmond, VA (US)

(73) Assignee: Virginia Commonwealth University, Richmond, VA (US)

( * ) Notice: Subject to any disclaimer, the term of this patent is extended or adjusted under 35 U.S.C. 154(b) by 0 days.

(21) Appl. No.: 14/783,450

(22) PCT Filed: Mar. 12, 2014

(86) PCT No.: PCT/US2014/023945
§ 371 (c)(1),
(2) Date: Oct. 9, 2015

(87) PCT Pub. No.: WO2014/168708
PCT Pub. Date: Oct. 16, 2014

(65) Prior Publication Data
US 2016/0051815 A1 Feb. 25, 2016

Related U.S. Application Data

(60) Provisional application No. 61/810,320, filed on Apr. 10, 2013.

(51) Int. Cl.
*A61N 1/36* (2006.01)
*A61N 1/05* (2006.01)
*A61N 1/372* (2006.01)

(52) U.S. Cl.
CPC .......... *A61N 1/3606* (2013.01); *A61N 1/0531* (2013.01); *A61N 1/0546* (2013.01); *A61N 1/3601* (2013.01);

(Continued)

(58) Field of Classification Search
CPC .. A61N 1/0531; A61N 1/0546; A61N 1/3601; A61N 2001/36039; A61N 2001/36057; A61N 2001/3606
See application file for complete search history.

(56) References Cited

U.S. PATENT DOCUMENTS 6,374,140 B1 * 4/2002 Rise ................... A61N 1/36064
600/544
7,400,927 B1 * 7/2008 Litvin ................ A61N 1/36025
128/898

(Continued)

OTHER PUBLICATIONS

Coelho DH, Costanzo RM. "Spatial Mapping in the Rat Olfactory Bulb by Odor and Direct Electrical Stimulation." Otolaryngol Head Neck Surg. May 10, 2016. pii: 0194599816646358.*

*Primary Examiner* — Eugene T Wu
(74) *Attorney, Agent, or Firm* — Whitham, Curtis & Cook, P.C.

(57) ABSTRACT

The system includes five components: (1) a sensor array, (2) a processor, (3) a transmitter, (4) a receiver-stimulator, and (5) an implantable electrode array. The olfactory implant system generates odor fingerprints by detecting odors with an array of chemical sensors and then transmitting variable spatio-temporal stimulation patterns for an electrode array with electrode stimulating points positioned at different locations in the olfactory cortex (e.g., stimulating the olfactory bulb). Different patterns of activity in the olfactory cortex are thereby generated which mimic the sense of smell in a subject. Once trained the system should be usable by a subject to detect or correctly identify one or more odors.

18 Claims, 14 Drawing Sheets

(52) U.S. Cl.
CPC ....... *A61N 1/36128* (2013.01); *A61N 1/36153* (2013.01); *A61N 1/36167* (2013.01); *A61N 1/37211* (2013.01)

(56) References Cited

U.S. PATENT DOCUMENTS

| | | | |
|---|---|---|---|
| 2004/0152946 A1* | 8/2004 | Franck | A61N 1/08 600/25 |
| 2004/0229345 A1 | 11/2004 | Oka et al. | |
| 2006/0191319 A1 | 8/2006 | Kurup | |
| 2006/0206169 A1* | 9/2006 | Schuler | A61N 1/36007 607/58 |
| 2007/0179557 A1* | 8/2007 | Maschino | A61N 2/008 607/45 |
| 2008/0077192 A1* | 3/2008 | Harry | A61H 23/0263 607/48 |
| 2009/0044761 A1 | 2/2009 | Chapin et al. | |
| 2012/0197250 A1 | 8/2012 | Ward | |

* cited by examiner

OLFACTORY IMPLANT SYSTEM

BACKGROUND OF THE INVENTION

Field of the Invention

The present invention generally relates to prosthetic devices and, more particularly, to an olfactory implant system for individuals who have an impaired or lost sense of smell.

Background Description

Information is transmitted in the human body by the nervous system. Electrical pulses, or propagating action potentials, travel along the extensions (axons) of a nerve cell, from one nerve to another (or between many nerves) to create a functional network of communication. Electric pulses begin when the organs of sensation are stimulated. Olfaction, or the sense of smell, is controlled by the olfactory system comprising olfactory nerves. In humans, the odorant-detecting portions of the olfactory nerves are within the nasal cavity where they have exposure and therefore access to odor molecules which are inhaled by the subject. The nerves pass from the nasal cavity through the cribiform plate of the anterior skull base and synapse with 2nd order neurons in the olfactory bulb. In cases where a subject has a damaged or lost sense of smell, it is most commonly due to destruction or interruption of the olfactory nerves. The olfactory bulb in these circumstances usually remains intact and healthy.

Sensors and sensor arrays for the detection and identification of some airborne molecules are known and used to detect odor molecules which stimulate the human olfaction system as well as vapor molecules which humans may not have the ability to smell. Sensors of this kind, which are sometimes referred to as "electronic noses", are found in food, industrial, and environmental applications, for example. US Patent Publication No. 2006/0191319 to Kurup describes detecting soil born contaminants or volatile organic compounds in soil. This may be useful in areas where industry operations such as hydrocarbon extraction (e.g. hydraulic fracturing, or "fracking") are performed. Odor detection may be used by a food processing plant to help detect spoiled goods. Carbon monoxide detectors are commonly found in both commercial and residential environments as a safety precaution since humans cannot sense carbon monoxide, which can be lethal if large amounts are inhaled.

Stimulating devices and techniques for electrical stimulation of particular tissues of the human body are also known. U.S. Pat. No. 3,236,240 to Bradley is a very early US patent pointing to stimulation of muscle tissue, in this case the muscles controlling the bladder. Many modern stimulatory applications have been directed to interacting more closely with the central nervous system. Deep brain stimulation, for example, may involve a small linear array of stimulating electrodes which are implanted to provide small low power electrical fields in selected regions of the brain. This has been successfully used for maladies from Parkinson's Disease to depression.

Cochlear implants are another well-known biostimulatory application. A stimulating electrode array is implanted into the human cochlea to artificially trigger action potentials in the human auditory nerves for persons who have impaired or lost capacity for hearing. Electrode arrays have been used with the central nervous system; at the end organs (cochlea, eye, brain, kidney, liver, stomach, muscle or other tissue, for example); and along the nerve pathways, both afferent and efferent, of the peripheral nervous system which bridge the central nervous system with the end organs. Unfortunately not all five human senses are treatable by bioelectrical stimulation means or otherwise in the case of lost or impaired function. For anosmics, or persons who have lost their sense of smell due to injury or disease, there is currently no known means for recreating this important sense.

SUMMARY OF THE INVENTION

An exemplary embodiment of the present invention is to provide a system and method to recreate, simulate, and/or mimic a sense of smell in a subject.

It is another exemplary embodiment of the present invention to provide a system that permits direct implantation and interfacing with the olfactory centers of the brain, the olfactory bulb as a particular example, for a renewed or improved perception of smell.

According to the present invention, these and other embodiments and advantages are achieved in an olfactory implant system including: (1) a sensor array, (2) a processor, (3) a transmitter, (4) a receiver-stimulator, and (5) an implantable electrode array. The olfactory implant system generates odor maps by detecting odors with an array of chemical sensors and then transmitting variable spatio-temporal stimulation patterns by an electrode array with electrode stimulating points positioned at different locations about the olfactory bulb or other part of the olfactory cortex. Different patterns of activity in the olfactory cortex are thereby generated which mimic the sense of smell in a subject. Once trained the system should be usable by a subject to detect or correctly identify one or more odors.

BRIEF DESCRIPTION OF THE DRAWINGS

The foregoing and other objects, aspects and advantages will be better understood from the following detailed description of a preferred embodiment of the invention with reference to the drawings, in which.

DETAILED DESCRIPTION

Figure 1:
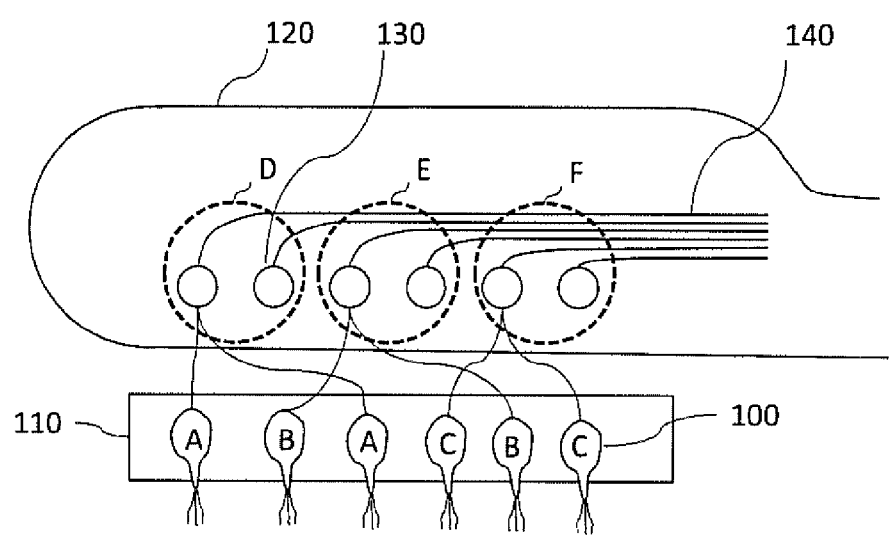
FIG. 1 shows basic neurophysiology of an olfactory system.

Referring now to the drawings, and more particularly to FIG. 1, there is shown a schematic of basic neurophysiology of the human or animal olfactory system.

Olfactory receptors 100 located in the olfactory epithelium 110 line the nasal cavity. When volatile or airborne substances bind to olfactory receptors 100 capable of receiving one or more particular airborne ligands, olfactory information from the activated odorant receptors 100 is passed to localized regions in the olfactory bulb 120. In particular, the projecting nerve fibers have dendrites which synapse onto particular well-defined microregions of the olfactory bulb 120 called glomeruli 130. Although the receptors 100 for a given ligand or family of ligands appear dispersed with little spatial organization across the olfactory epithelium, the nerve endings from the same receptors 100 converge on the same glomerulus. Different receptor subtypes (e.g. A, B, and C) connect to or associate with specific glomeruli 130 within localized regions (e.g. D, E, and F) of the olfactory bulb 120. The information from the receptors creates unique spatial neurological activity patterns of neural activity for different odors. These patterns are called odor maps. Different chemicals generate different patterns of neural activity. As stimulation of the receptors occurs in continuous time, the odor maps are spatio-temporal patterns in the olfactory bulb 120 which provide the olfactory system means to reproducibly discriminate between different odors. The neural activity patterns in the olfactory bulb 120 are transmitted to higher levels of the brain via second order mitral cell nerve fibers that make up the olfactory tract 140. Unique spatial neurological activity patterns of neural activity for different odors (i.e. odor maps) are not limited to the olfactory bulb 120. Odor maps of nervous system structures additional to the olfactory bulb, in particular regions and parts of the olfactory cortex, may be utilized in accordance with the invention. As used herein, "olfactory cortex" is meant to include, but is not limited to, one or more of olfactory bulb, amygdala, pyriform cortex, orbitofrontal cortex, olfactory turbercle, and the entorhinal cortex. While some exemplary embodiments herein discuss stimulation of the olfactory bulb in particular, these are but illustrative examples, and one or more other parts of the olfactory cortex may alternatively or additionally be stimulated as described for simulation or mimicking an odor.

Figure 2:
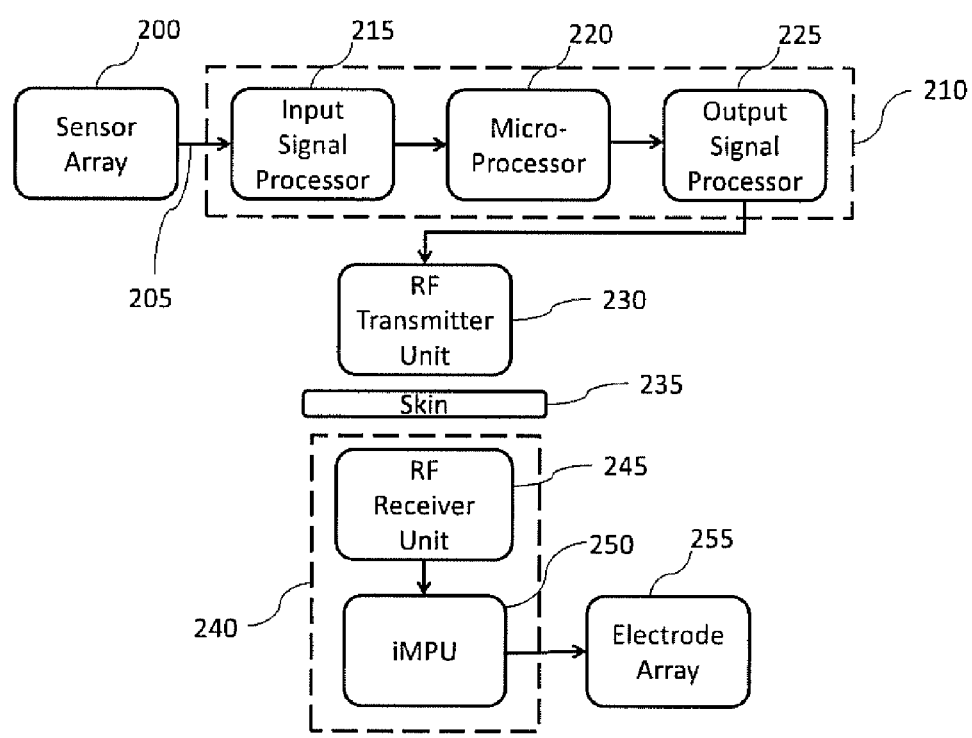
FIG. 2 is a schematic of an olfactory implant system.

Referring now to FIG. 2, an olfactory implant system for use with a human or animal olfactory system such as that which is illustrated in FIG. 1 includes one or more sensors or a sensor array 200, one or more processors 210, one or more transmitters 230, one or more receiver-stimulators 240, and one or more implantable electrode arrays 255. One or more vapors from a subject's surrounding environment is detected with sensor array 200. Sensor array 200 produces sensor output signals 205 in response to detecting one or more vapors of a possible plurality of vapors. Processor 210 processes the sensor output signals 205 into digital encoded information. Processor 210 can include an input signal processor 215 which digitizes the analog sensor output signals, one or more microprocessors 220, and an output signal processor 225 which provides digital encoded information. Transmitter 230, which may be an RF or other wireless transmitter, transcutaneously transmits the digital encoded information across the skin 235 of the subject to a receiver-stimulator 240. Receiver-stimulator 240 can include receiver 245, which may be an RF or other wireless receiver to communicate with transmitter 230, and one or more implant processors or internal microprocessing units (iMPUs) 250 which generates electrical impulses as a function of the digital encoded information. Implanted electrode array 255 includes at least one stimulating electrode for stimulating the olfactory bulb in the subject with the electrical impulses. The electrical impulses may be associated with spatio-temporal electrical stimulation patterns which mimic the effect of the naturally occurring spatio-temporal electrical stimulation patterns of the olfactory system. Unless otherwise noted, 'simulate', 'mimic', 'recreate', and 'restore' (with reference to the sense of smell) are treated herein as functionally equivalent and may be used interchangeably herein.

Figure 3:
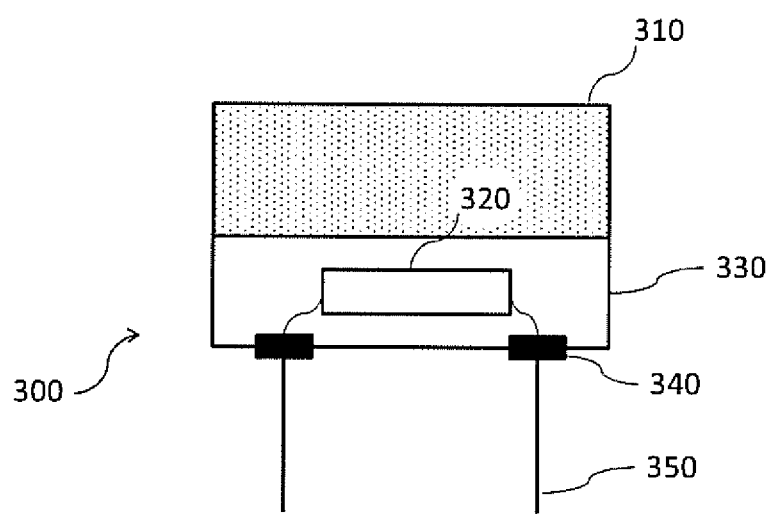
FIG. 3 is a schematic of a single odor sensor.
Figure 4:
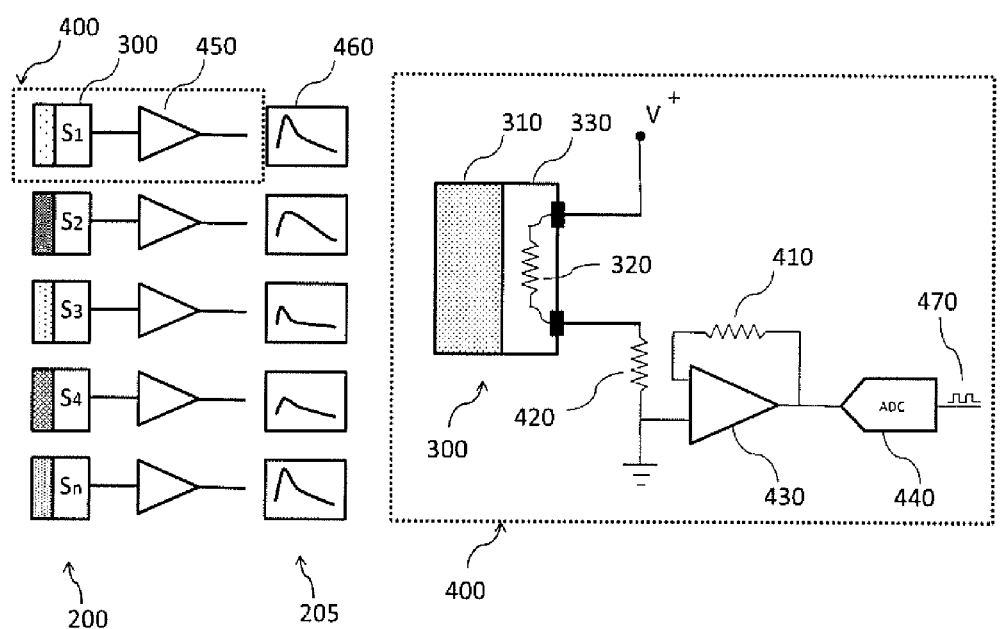
FIG. 4 shows a sensor array comprising a plurality of odor sensors, analog output signals therefrom, and control circuitry.

Referring now to FIGS. 3 and 4, odor stimuli are detected by sensor(s) 300 or sensor array 200 having a plurality of individual sensors ($S_1$, $S_3$, $S_4$, . . . , $S_n$). Each sensor 300 is configured to detect and respond to at least one molecule or group of molecules sharing certain chemical properties in vapor form, hereafter referred to as a 'target vapor' or 'target molecules'. 'Odor' and 'vapor' are used equivalently herein, as are 'odor molecule', 'chemical', and 'vapor molecule', unless noted otherwise. 'Vapor' as used herein is meant to indicate any collection of airborne molecules or particles which evoke/cause a particular response by the olfactory implant system. The opposite, a 'nontarget vapor', is therefore any collection of airborne molecules or particles which have no significant effect upon the response or behavior of the sensor array. As such, a 'target vapor' may be a pure vapor comprising a plurality of molecules all having the same chemical formula, or it may be a mixed vapor comprising a plurality of molecules of different chemical formulae the combination of which produces a sensor array response which is different from the sensor array response to one or more of the chemical formulae provided individually. A group of target molecules may share, for example, similar binding/ligand properties or rates of diffusion through a filter. When target molecules interact with the surface of a sensor 300 they change the conductivity of the sensor and alter the amount of current that is detected. In some embodiments filters 310 that impede the access of chemicals may be used to modify the selectivity of different sensors so that different chemicals produce different sensor array outputs 205.

Each sensor 300 or grouping of sensors of a sensor array 200 may be configured to be sensitive only to a particular target vapor. In an embodiment, a sensor array 200 comprises a plurality of groupings of one or more sensors, where each grouping is configured to detect a different vapor. Alternatively, each sensor 300 may have sensitivity to a plurality or range of vapors. Still as a further alternative, a sensor array of identical sensors can be modified to include a different filter on each sensor to distinguish different vapors. FIG. 3 shows an exemplary embodiment of an odor sensor 300 which includes a filter 310, a conducting element 320 that changes its resistance to current flow when exposed to target molecules, lead wire attachment sites 340, and pin connectors 350. Conducting element 320 is within sensor compartment 330.

A sensor array 200 shown in FIG. 4 illustrates an embodiment which has a plurality of identical sensors 300, but with each sensor having a different filter 310. In some embodiments each filter differentially affects the passage or flow of different molecules across the filter. For example, this could be a form of active regulation or alternatively could be a form passive regulation, such as absorption or diffusion at different rates for different vapor molecules. Each sensor therefore has a different reaction/sensitivity to the different vapor molecules. As a result, one or more sensors may give a different response profile for a given vapor which can be associated with a unique odor fingerprint.

Filter 310, which may also be referred to as a selectivity filter, may be fixedly attached to the sensor or integrally formed thereon. In an embodiment the filter may selectively absorb a target vapor, such that the target molecules have a different (e.g. faster) rate of diffusion through the filter than do non-target molecules. A filter-sensor pair is preferentially sensitive or tuned to a particular odor molecule or group of odor molecules. The number of sensors and the number of target vapors which the sensor array detects may be variable, for instance as low as 1 or as high as numbering in the thousands, depending on the desired resolution of the system. In an alternative embodiment, the filter for each sensor could selectively block some molecules while permitting one or more other molecules to pass. One skilled in the art would recognize a variety of considerations may be made in selecting the resolution of the sensor array, such as cost of materials, size of the device, and complexity of the device. Furthermore, while FIGS. 3 and 4 show the use of filters, a sensor array without filters could be employed in the practice of the invention.

Target vapors to which the sensor array is sensitive can vary depending on the intended use of the olfactory implant system. For improving quality of life to an anosmic, target vapors may include molecules commonly associated with forms of pleasure or gratification, including molecules associated with food or fragrances, such as amyl acetate (banana), ethyl butyrate (fruity,pineapple), ethyl valerate (apple), citral (lemon), d-limonene (orange), and phenyl ethyl acetate (rose), or molecules associated with the outdoors, such as decyl methyl ether (fresh air), hexyl benzoate (woody, pine), and iso propyl quinolone (earthy, woody). Personal safety may be improved with target vapors including t-butyl mercaptan (rotten egg smell added to natural gas) or burnt wood or plastics (smoky), for example. Detection of these vapors may alert a user to the presence of harmful or dangerous substances in the environment, such as smoke or fire. Sensitivity to methane, for instance, could alert a user to the presence of a gas leak. In some embodiments target vapors may include vapors for which humans naturally have no sensitivity. That is to say, the sensor array is not limited to detection of odors which the natural human olfactory system is capable of detecting. It may include sensitivity to carbon-monoxide, for instance, to provide awareness of the presence of this harmful vapor in the surrounding air.

FIG. 4 shows a sensor array 200 having multiple sensors 300 and operational amplifiers circuits 450, where the analog waveforms generated or produced from each of the sensors are provided as sensor output signals. An exemplary sensor module 400 including sensor 300 shows filter 310, sensor compartment 330, conducting element 320, feedback gain resistor 410 for operational amplifier 430, load resistor 420 and analog to digital converter 440 that may digitize the waveform (see ADC output 470).

One of ordinary skill in the art will recognize that known sensor arrays and even processing for existing sensor arrays may be used in the practice of the invention. In an alternative embodiment, a commercially-available sensor array for detecting vapor molecules may be adapted for use with the present invention. An exemplary sensor array for this purpose would be Cyranose Electronic Nose manufactured and sold by Intelligent Optical Solutions (California, USA). The Cyranose Electronic Nose is a handheld package which may use different types of sensor (e.g. for $CO_2$, $H_2S$, $O_2$, or VOCs) and can include a database of digital images or "smellprints" for known vapors and perform best match comparisons between existing "smellprints" and unknown vapors.

One additional example of a sensor array which could be adapted for use with the present invention is an "electronic nose" being developed by the National Institute of Standards and Technology (NIST) having 16 microheater elements and eight types of sensors coupled with a pattern-recognition module. A description of the NIST "electronic nose" is available online at the institute's website in an article titled 'Sniffing Out a Better Chemical Sensor'.

Figure 5:
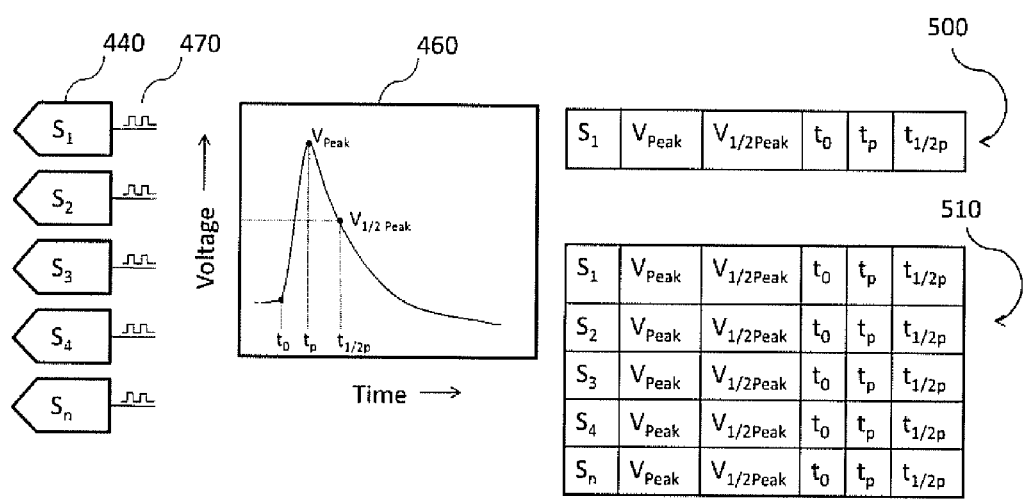
FIG. 5 shows response parameters usable for generation of odor fingerprints.
Figure 6:
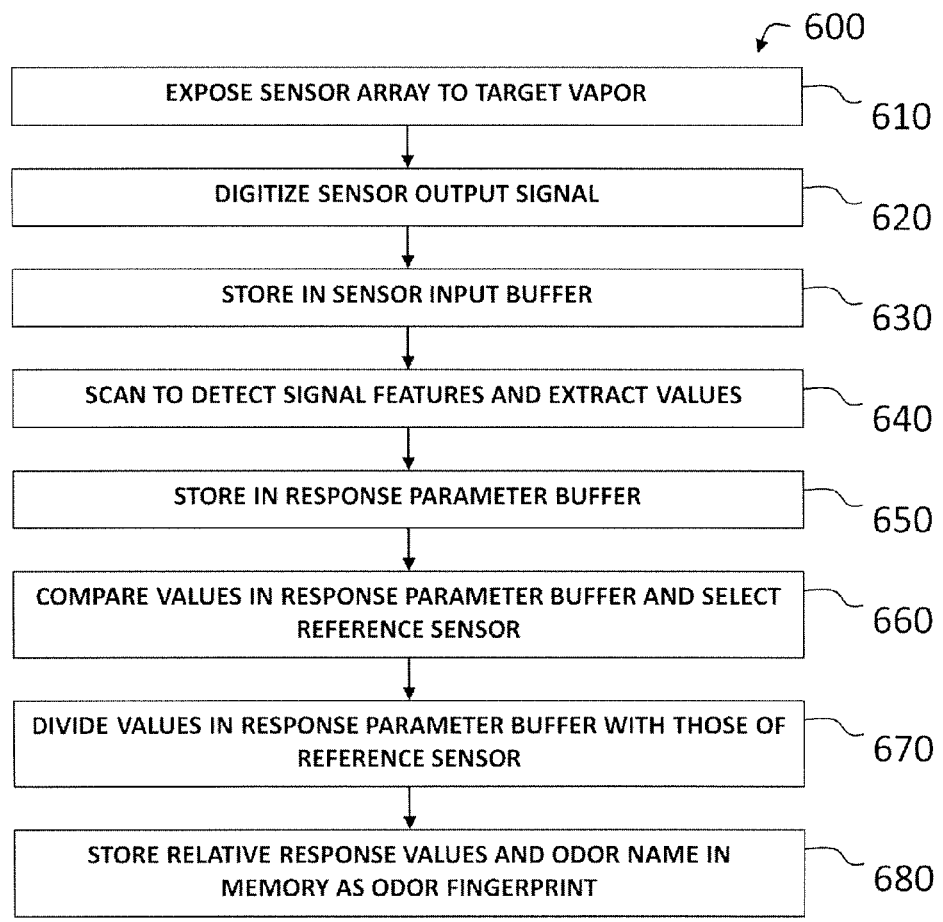
FIG. 6 is a flow diagram of a process for generating a lookup table of odor fingerprints.

FIG. 5 shows a schematic illustrating response parameter detection and extraction for generation of odor fingerprints. FIG. 6 shows a process for generating a look-up table of odor fingerprints. After the sensor array is exposed/subjected to a target vapor (see step 610 of process 600) sensor output signals 205 from the sensors ($S_1$ to $S_n$, any one of which may be generically identified as $S_x$) in sensor array 200 are digitized (see step 620) into digitized waveforms and stored as data in one or more sensor input buffers in processor 210 (see step 630). Digitization may be performed individually by an analog-to-digital converter 440 associated with an individual sensor, as shown in sensor module 400 which produces digitized waveforms 470 as output. Alternatively, digitization may be performed by one or more input signal processors 215 associated with processor 210. Digitized waveforms 460 are scanned to detect specific response parameters 500, for example (but not limited to) peak voltage ($V_{Peak}$), half peak voltage ($V_{1/2Peak}$), time to peak voltage ($t_p-t_o$), slope, rise time, area under the curve, and time to half peak voltage ($t_{1/2p}-t_o$), the values of which are extracted (see step 640) and stored in a response parameter buffer 510 (see step 650). Values for the response parameters of each of the sensors are compared and the sensor with the largest peak voltage ($V_{Peak}$) is selected as a reference sensor ($S_{ref}$) (see step 660). A sensor in the sensor array may be arranged without a filter. It could therefore have the largest peak voltage and be used as a common reference sensor for most or all iterations of process 600. Values for response parameters 500 stored in the response parameter buffer 510 are divided by the corresponding response parameter values associated with the reference sensor ($S_{ref}$) to obtain final relative response values ($S_x/S_{ref}$) for sensors 1 to n (see step 670). All relative response values associated with the same sensor ($S_x$) are stored in memory together with an identifier (e.g. a name, label, or chemical formula) which identifies the target vapor to which the sensor array was exposed (see step 680). This data set for the target vapor is referred to as an odor fingerprint. A plurality of odor fingerprints are generated and stored for a plurality of target vapors which the olfactory implant system is configured to detect.

Preferably, a receiver-stimulator 240 and electrode array 255 may be implanted in the subject. The receiver-stimulator may include receiver 245 and an internal micro-processor unit (iMPU) 250. The receiver-stimulator 240 may be implanted or positioned anywhere in the body, including both intracranial and extracranial locations. Examples include but are not limited to behind the subject's ear, in the chest (such as done with pacemakers), and in subcutaneous tissues of the scalp. In some embodiments, a receiver-stimulator 240 may be adjacent to or even incorporated with the electrode array. In still other embodiments, a receiver-stimulator 240 may be percutaneous and not require transcutaneous signal transmission by a transmitter 230. A receiver-stimulator 240 may be connected by direct electrical wiring or by wireless communications to an electrode array 255 which is implanted next to the olfactory bulb or another part of the olfactory cortex.

Figure 7:
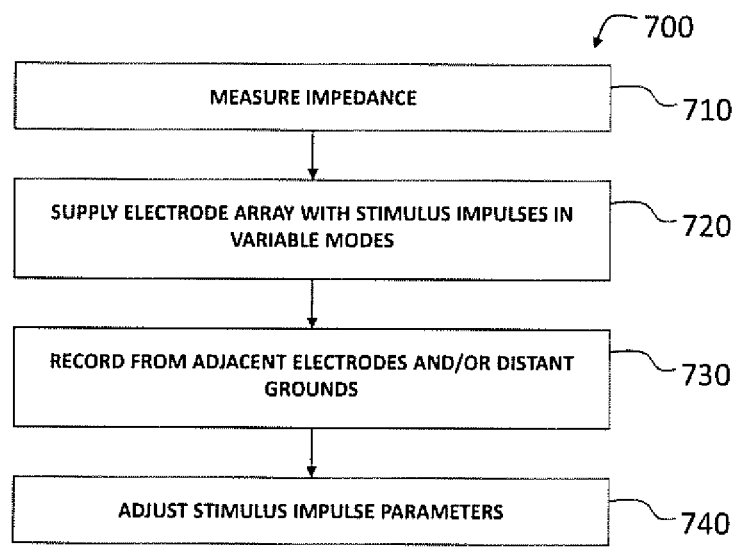
FIG. 7 is a flow diagram of a process for testing an electrode array.

FIG. 7 shows an exemplary process 700 for testing of the electrode array to ensure proper functionality and performance. Electrode integrity is tested by measuring impedance (see step 710). In a single iteration of what can be an iterative testing process, the electrode array is supplied with stimulus impulses of one of a plurality of variable modes (see step 720), the effects of which are measured and recorded from either adjacent recording electrodes and/or distant grounds (see step 730). The stimulus impulse parameters are adjusted to a different mode (see step 740) and some or all of the steps of process 700 may be repeated. The variable modes of step 720 may be variations on stimulation variables/parameters such as timing, amplitude (e.g. 0-500 µA), pulse duration (e.g. 5-1000 ns), frequency (e.g. up to 5000 Hz), and stimulation mode (e.g. bipolar). Each electrode in the electrode array is preferably individually controllable/programmable. Alternatively, electrodes may be grouped into units which are controlled together.

The electrode array may have recording electrodes in addition to stimulatory electrodes, or it may have electrodes which can serve either purpose depending on their configuration settings. For feedback, at least one recording electrode may be provided for recording one or more bioelectric properties (e.g. electric field properties) at the olfactory bulb in the subject. The recording electrode or electrodes may be separate from or an integral part of the stimulating electrode array. The recordings from the recording electrodes may be used to adjust stimulus impulse parameters as a function of the bioelectric properties.

One or more ground or reference electrodes for the electrode array may be arranged within a casing of a receiver-stimulator, for example, and/or placed in any other soft tissue location of the body, in which case the electrode may be provided with a conducting wire from the receiver-stimulator separate from conducting wires of the main electrode array positioned at the target stimulation site (e.g. the olfactory bulb). The use of a distant ground electrode is comparable to the use of distant ground electrodes with some cochlear implants.

Figure 8:
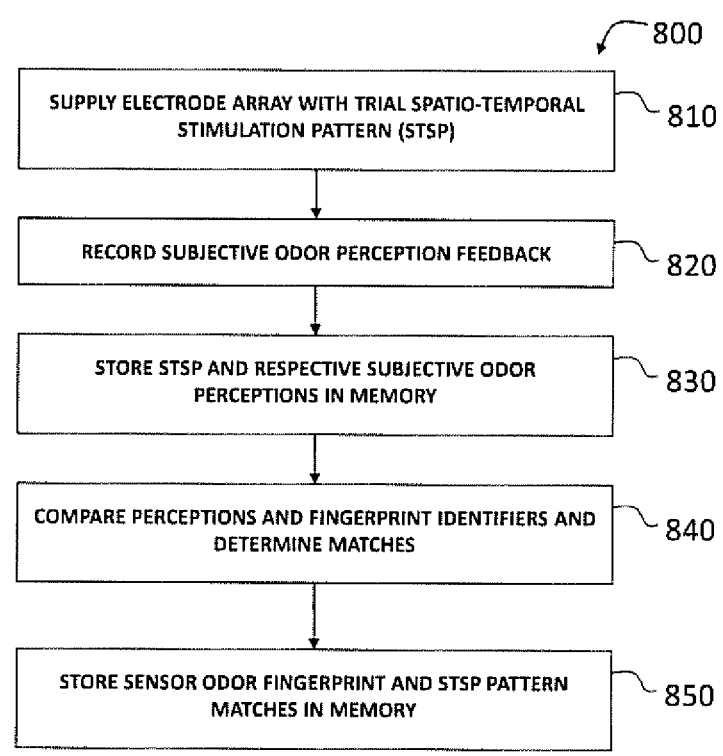
FIG. 8 is a flow diagram of a process for stimulation programming for training an olfactory implant system.

FIG. 8 shows an exemplary process 800 for stimulation programming for training an olfactory implant system of the present invention for optimized performance customized for the individual user. The electrode array is supplied with a first trial spatio-temporal stimulation pattern (STSP) (see step 810) with settings such as those stated above for testing of the array. The subjective odor perception from the subject's feedback is recorded (see step 820), and the subjective odor perception feedback is recorded together with the STSP parameters in memory (see step 830). This process is repeated with different STSP parameters multiple times to generate a library of subject odor perceptions and the electrical stimulation features which may be used to reproduce the perceptions. In an exemplary embodiment, stimulating the olfactory bulb, olfactory tract, or other part of the olfactory cortex in the subject with a first spatio-temporal electrical stimulation pattern simulates or mimics a first odor in the olfactory bulb, olfactory tract, or other part of the olfactory cortex in the subject, while stimulating the olfactory bulb, olfactory tract, or other part of the olfactory cortex with a second spatio-temporal electrical stimulation pattern which is different from the first spatio-temporal electrical stimulation pattern simulates or mimics a second odor in the olfactory bulb, olfactory tract, or other part of the olfactory cortex in the subject which is different from the first odor. That is to say, each spatio-temporal electrical stimulation pattern may simulate or mimic a unique odor/perception of an odor. Perceptions as reported by the subject can be compared with the identifiers of stored odor fingerprints and matches determined (see step 840). Matches may be stored in a non-volatile, computer-readable memory/storage medium (see step 850).

Figure 9:
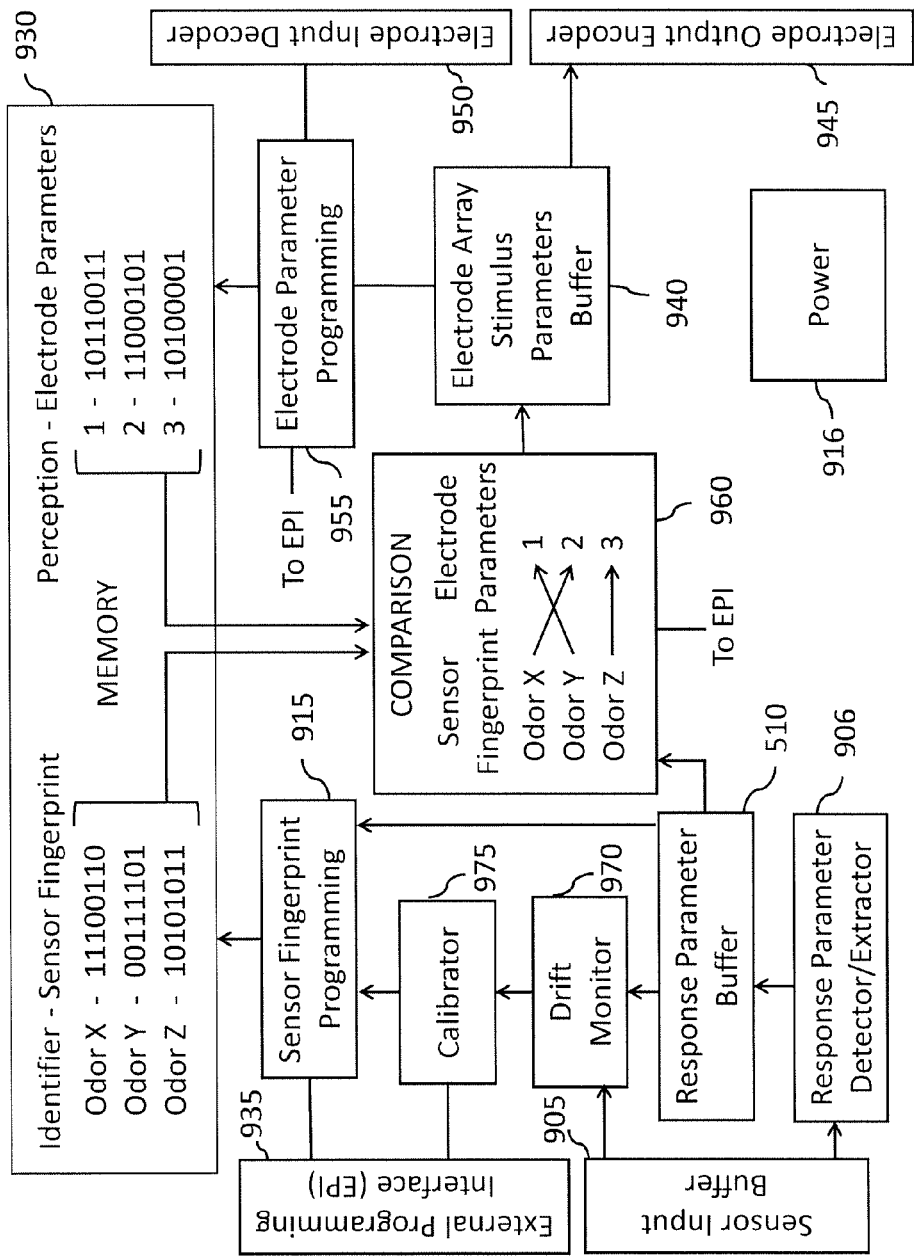
FIG. 9 is a schematic diagram of an exemplary embodiment of a processor or processor system which may be used in the olfactory implant system.

FIG. 9 shows an external micro-processor unit (eMPU), which is equivalent to processor 210 shown in FIG. 2. The eMPU 210 preferably performs several functions. These functions may be a subset of or all of the steps of processes 600, 700, and 800. It processes the sensor output data digitized and temporarily stored in one or more sensor input buffers 905. Detection and extraction of response parameters 500 may be performed by a response parameter/extractor circuit 906 and temporarily stored in response parameter buffer 510. The eMPU 210 may use the data temporarily stored in response parameter buffer 510 to perform sensor fingerprint programming 915 according to process 600. The eMPU may also or alternatively use the stored response parameters for comparison to stored subject perceptions in order to determine an electrode stimulus suitable for mimicking the detected vapor. Odor identifiers and their respective odor fingerprints are programmed into memory 930 after exposing the sensory array to a target vapor/odorant and then storing the odor fingerprint in memory along with one or more identifiers keyed in from an external programming interface 935, such as a computer. The eMPU and data stored in memory 930 may be programmed and accessed by an external programming interface (EPI) 935. Power may be supplied to components of the system by a power source 916 such as one or more commercially available batteries such as hearing aid batteries or rechargeable batteries.

A comparison circuit 960 associated with microprocessor 220 compares odor fingerprint identifiers stored in memory 930 with the subjective odor perceptions also stored in memory and determines matches (see step 840 of process 800). For each match, the comparison circuit 960 links the odor fingerprint with the corresponding STSP parameters which will generate an intended odor perception. During stimulation programming, matches are stored in memory 930 (see step 850 of process 800). During regular use of the system, a best match is used to determine the electrode array stimulus parameters which may be temporarily stored in a buffer 940 before being sent to an electrode output encoder 945 which supplies the electrode array with the stimulatory impulses which can be used to generate a sensation in the olfactory bulb.

Recording electrode signals from recording electrodes can arrive at the processor at electrode input decoder 950 and the data used for electrode parameter programming 955 according to process 700 as described above.

In some embodiments, one or more matches between odor fingerprints and corresponding STSP parameters/odor perceptions may be manually determined or overridden (such as by a user) in order for a given odor fingerprint to yield a different odor perception than might otherwise be expected. This allows a user to choose a matching at his/her discretion. As an example, a system may be arranged in which, under normal conditions, detection of a potato odor generates a stimulatory pattern which simulates or mimics a first odor. Detection of an apple odor, on the other hand, generates a stimulatory pattern which simulates or mimics a second odor which is different from the first odor. A user or authorized administrator (e.g. a doctor) may configure the system (at, for example, a processor or receiver-stimulator) such that detection of a potato odor generates a stimulatory pattern which simulates or mimics the second odor (that which was matched with apple) instead of a stimulatory pattern which simulates or mimics the first odor (that which was matched with the potato). Thus, the user would have the perception normally associated with apple odor now associated with both apple odor and potato odor. In effect, one or more matchings between odor fingerprints and stimulatory patterns providing particular odor perceptions may be adjusted or changed, either permanently or temporarily.

In some embodiments, a stimulatory pattern may be generated in response to entry of a command or instruction from a user (received at, e.g., an external programming interface) with or without detection of an odor fingerprint regularly associated with that stimulatory pattern. For example, despite an odor from an apple not being present and therefore not being detected by the sensor array, a user may command or instruct the implant system to nevertheless stimulate the olfactory cortex (e.g. the olfactory bulb) with the STSP parameters which simulate or mimic the perception of apple. This feature may be desirable if, for example, a user is consuming a bland food and selective simulation or enhancement of a food aroma is desired. An input from the user can be received by the implant device which prompts stimulation such that one or more aromas not appreciably present from the food are perceived by the user. A user may choose which aroma or aromas are simulated.

As with all measuring instruments, fluctuations and deviations of signal readings (i.e. "sensor drift") are to be expected over time, especially as the sensors age. As such, processor 210 may include a drift monitor 970 to monitor and identify fluctuations or gradual changes in the behavior/signal outputs of the sensors over time, as shown in FIG. 9. The monitor can compare one or more of the analog sensor output signals, the digitized sensor output signals stored in sensor input buffer 905, and the response parameter values stored in response parameter buffer 510 for a target vapor with the odor fingerprint stored in memory. Processor 210 may furthermore comprise a calibrator 975 which accounts for fluctuations or gradual changes in the electrical characteristics and/or sensitivity of the sensors of the sensor array. One skilled in the art will recognize that this may be done in a variety of ways. Calibrator 975 may adjust the fingerprint database in memory 930 by sensor fingerprint programming 915. Alternatively, calibrator 975 may store a quantitative record of sensor drift in memory which could be used as an additional variable by comparison circuit 960. The drift monitor 970 may be configured to communicate with the calibrator 975 to automatically adjust for fluctuations or changes. The drift monitor and calibrator may also be integral with one another and/or integral with sensor fingerprint programming 915. In some embodiments, the drift monitor and/or calibrator may be in communication with an external programming interface 935 which allows user access and/or configuration of the drift monitor and calibrator.

Processing of sensor output signals may include the steps of detecting a first electrical profile from the sensor output signals, extracting one or more values describing that electrical profile, comparing one or more of the extracted values with one or more values of at least one other electrical profile of a known vapor, and generating digital encoded information associated with at least one of the other electrical profiles of known vapors which the processor has matched with the detected electrical profile. Electrical profiles may be of current, resistance, voltage, or impedance over time, for example.

Figure 10:
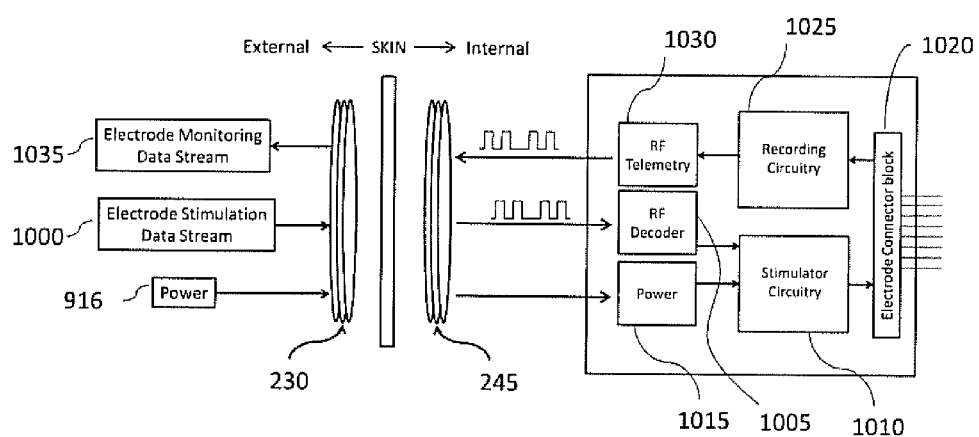
FIG. 10 shows diagrams of exemplary embodiments of a transmitter and a receiver-stimulator.

FIG. 10 illustrates how data is transferred between eMPU 210 and iMPU 250 by wireless signals across the skin (e.g. radio frequencies). An output of processor 210, which is an electrode stimulation data stream 1000 representing the STSP parameters for an odor perception, is sent to transmitter 230 and converted to radiofrequency (RF). The data stream 1000 can be encoded (including, for example, digital to analog conversion) by an electrode output encoder 945 before wireless transmission. The RF signal is fed to an amplifier. RF decoder 1005 associated with iMPU 250 decodes the digital data stream into instructions for electrode stimulation. Stimulation variables (e.g. onset, current intensity, pulse duration, interpulse interval, number of pulses) at each electrode in the array are set by the iMPU 250 according to electrode array stimulus parameters for the different odor perceptions experienced by the subject. Current level is controlled by a digital to analog convertor which is a part of stimulator circuitry 1010. The stimulator circuitry is comprised of amplifiers and timing circuits that control both the stimulus intensity (current levels) and the pulse parameters (duration, inter pulse intervals, and number of pulses) that is sent to each of the electrodes.

A primary (external) inductor associated with transmitter 230 transmits energy wirelessly to a secondary (internal) inductor associated with receiver 245. The two inductors may be kept in alignment by magnets within the center of each. A capacitor can be used to create resonance. The generated power at the secondary inductor can be rectified using a full wave rectifier and the energy stored in power module 1015. This power is used to operate the receiver-stimulator and to provide current needed to send stimulus pulses to the electrodes at an electrode connector block 1020 output of the iMPU 250. Power is preferably supplied to power module 1015 by power source 916. Power is also used for recording circuitry 1025 which may send electrode monitoring data encoded by the iMPU back to the eMPU by RF telemetry 1030. The recording circuitry is comprised of amplifiers and analogue to digital converters (ADCs) that processes the voltage changes detected at each of the electrodes and sends them to the RF telemetry circuits. Transmitter 230 sends an electrode monitoring feedback data stream 1035 to processor 210 where it can be decoded (including, for example, analog to digital conversion) by electrode input decoder 950.

Figure 11:
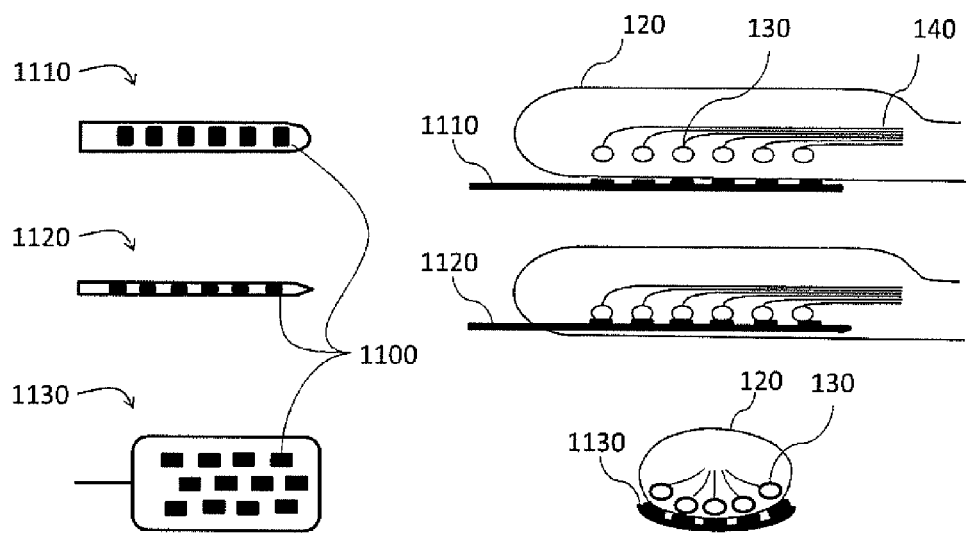
FIG. 11 are schematic diagrams of electrode arrays.

FIG. 11 shows three different electrode arrays used to stimulate the olfactory cortex in different ways. One or more olfactory bulbs 120, one more olfactory glomeruli 130, and/or one or more olfactory tract nerve fibers 140 may all be stimulated by varying the shape of electrode contact region 1100. This may be accomplished with a straight electrode array 1110, a penetrating electrode array 1120, and/or a pad/panel electrode array 1130. Other regions or parts of the olfactory cortex may likewise be stimulated with an electrode array. Such other parts of the olfactory cortex include, but are not limited to, the amygdala, the pyriform cortex, the orbitofrontal cortex, the olfactory turbercle, and the entorhinal cortex. A particular stimulation target of the olfactory cortex may be selected for various reasons. For example, some regions are more accessible by known surgical implant methods and may therefore involve less complicated medical procedures. One or more particular stimulation targets may also be selected according to the desired resolution of the physiological response. The amygdala, pyriform cortex, and orbitofrontal cortex may, for example, be particularly well suited for stimulation by an electrode array according to their respective spatial neurological activity patterns of neural activity for different odors (odor maps). As was previously indicated, the olfactory bulb is just one exemplary target for stimulation.

An exemplary electrode array is a flexible pad electrode array. This allows for the array to be configured about the three-dimensional surface of an olfactory bulb 120 with each electrode 1100 touching or immediately adjacent to the surface of the bulb. The size of the array is dependent on the size of the olfactory bulb of the subject. In humans, an adult olfactory bulb measures about 10 mm by 2 mm. Glomeruli are about 0.1 mm in diameter. The array may contain as many as 64 electrodes. However, fewer electrodes may be chosen to reduce cost or for other considerations and in some cases even improve performance of the device. The electrode array stimulates the olfactory bulb according to a particular spatio-temporal stimulation pattern which mimics a sense of smell of a particular odor in the central nervous system of the subject.

The electrode array may be a custom array designed specifically for the present invention. Alternatively, the electrode array may be commercially acquired from an existing manufacturer for stimulatory devices such as cochlear implants. One example of a commercial source for an electrode array which may be used in accordance with the present invention is NeuroNexis (the home website of which is neuronexistech.com as of Apr. 1, 2013). NeuroNexis offers catalog surface electrode arrays and penetrating electrodes, for example, in addition to customized electrode arrays.

Figure 12:
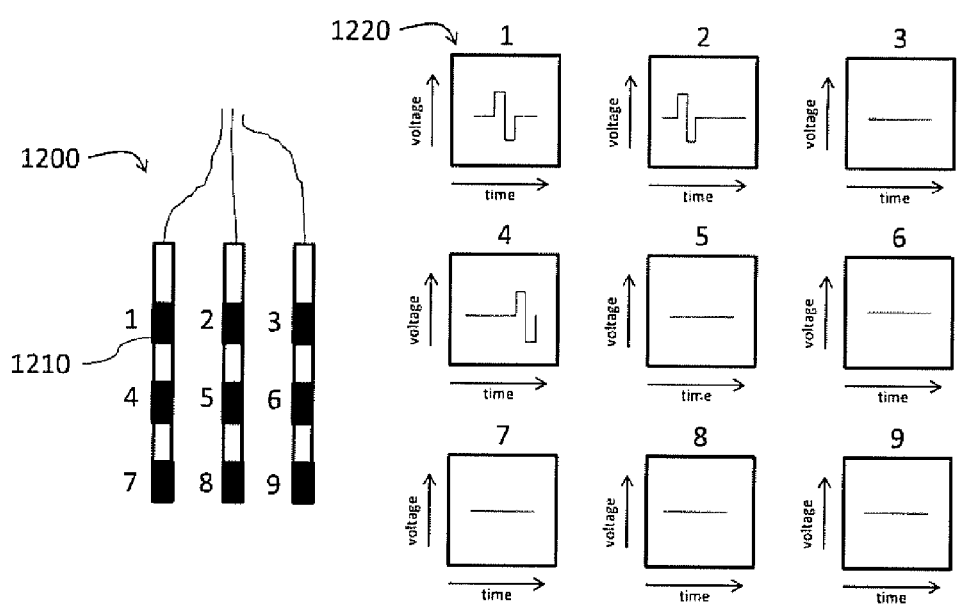
FIG. 12 shows a spatio-temporal stimulation pattern.

FIG. 12 is an example visual representation of a spatio-temporal stimulation pattern for a 3×3 electrode array. An electrode array 1200 is another embodiment of an electrode array which may be used in the practice of the invention. Electrode Array 1200 comprises three groups of three electrodes wherein each of the nine electrodes 1210 are preferably independently controllable. The nine voltage-time plots 1220 show the stimulation parameters for each electrode 1210. In this example, electrodes 1, 2, and 4 each are supplied a biphasic single stimulatory pulse of approximately equal magnitude and duration but having start times offset from one another. The remaining six electrodes are not supplied a stimulatory pulse. Each stimulatory electrode 1210 may be exclusively utilized for stimulation of a single glomerulus. Alternatively, one or more may be positioned to stimulate more than one glomerulus with equal or different intensity.

Figure 13A:
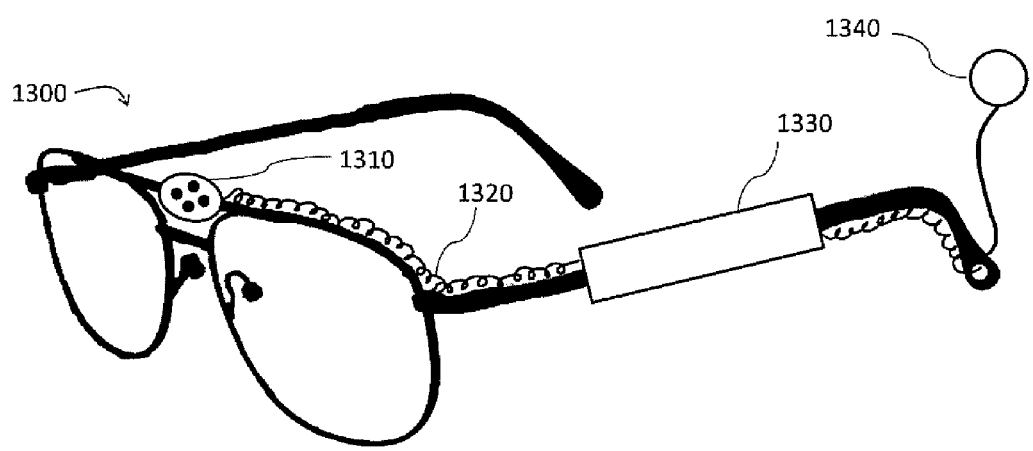
FIGS. 13A and 13B are diagrams of wearable devices.
Figure 13B:
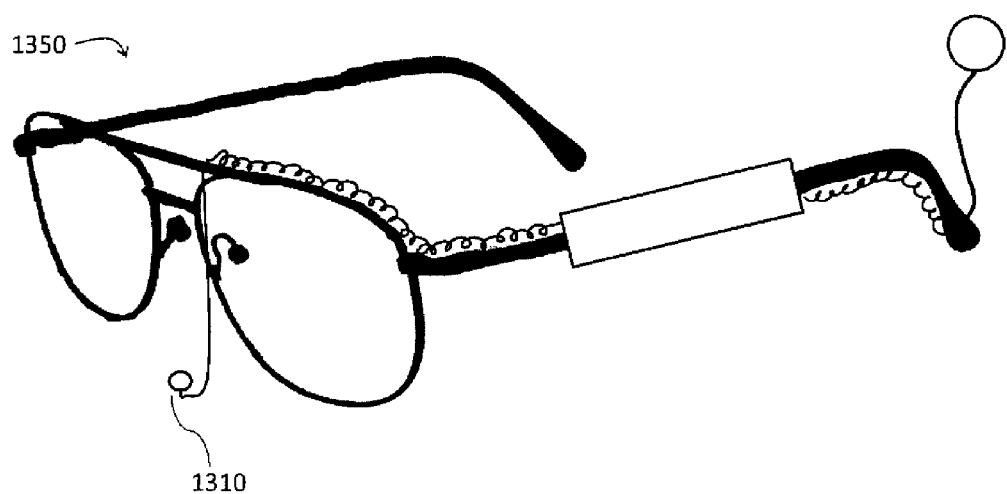

FIGS. 13A and 13B show diagrams of wearable modules which may be used for a subject to carry the external components of the present invention, including the sensor array, eMPU, and transmitter. In an exemplary embodiment as shown in FIG. 13A, sensor array 1310 may be attached to a pair of eyeglasses 1300 or safety glasses, such as on the bridge of the glasses. Sensor array 1310 may also be formed integrally therewith to improve the cosmetic appearance of the device, for example. As another alternative, FIG. 13B shows a sensor array 1310 which can be positioned under the external naris (nostril) of the nose. In this position vapors would pass across the sensors when the subject sniffs or inhales through the nose. Processor 1330 may likewise be fixedly or removably attached to the eyeglasses, such as on the temple or earpiece, or formed integrally therewith. Sensor array 1310 and processor 1330 may be connected such that the sensor array is in communication with the processor. When both components are disposed on a pair of eyeglasses they can be connected by wiring 1320. Alternatively, the sensor array and processor may be positioned at some distance to one another. The sensor array and/or processor could be attachable to a hat, for instance, or to a belt similar to a pager or a cell phone, in which case the sensor array may communicate wirelessly with the processor. Processor 1330 is shown connected to transmitter 1340 for transcutaneously transmitting digital encoded information to the implanted stimulator-receiver in the subject. In some embodiments, percutaneous transmission may also be used. This may be especially useful in research applications, for example.

While processing as described in FIGS. 5-9 has been disclosed as mostly or entirely taking place on board a processor 240, this represents only one exemplary embodiment of the current invention. Processing steps may be divided over a plurality of separate processors which may be external or internal (i.e. implanted in the subject). Processing steps may also be performed remotely, with the sensor array and/or receiver-stimulator in wireless communication with a processor which is not carried or worn by the subject. Furthermore, one of ordinary skill in the art will recognize that all necessary processing (for example, that which is performed by comparison circuit 960) may be performed by hardware, software (e.g. computer programs), firmware, or a wide range of combinations thereof and is not limited to the exemplary processor shown in FIG. 9.

The subjects which are the end-users of the methods and devices of the invention are generally mammals, and are usually humans. Veterinary applications of this technology are also contemplated.

While the invention has been described in terms of preferred embodiments, those skilled in the art will recognize that the invention can be practiced with modification within the spirit and scope of the appended claims.

Having thus described our invention, what we claim as new and desire to secure by Letters Patent is as follows:

1. A method for mimicking a sense of smell in a subject, comprising the steps of:
   detecting one or more vapors with a sensor array, said sensor array producing sensor output signals in response to detecting said one or more vapors;
   processing said sensor output signals into digital encoded information;
   transmitting said digital encoded information transcutaneously into said subject;
   generating electrical impulses as a function of said digital encoded information, wherein said electrical impulses are determined according to training conducted by a user; and
   stimulating the olfactory cortex in said subject with said electrical impulses with an implantable electrode array comprising at least one stimulating electrode.

2. The method as claimed in claim 1, wherein said electrical impulses are associated with spatio-temporal electrical stimulation patterns.

3. The method as claimed in claim 2, wherein stimulating the olfactory cortex in said subject with a first spatio-temporal electrical stimulation pattern simulates or mimics a first odor and stimulating the olfactory cortex with a second spatio-temporal electrical stimulation pattern which is different from said first spatio-temporal electrical stimulation pattern simulates or mimics a second odor which is different from said first odor.

4. The method as claimed in claim 1, wherein said processing step comprises the steps of:
   detecting a first electrical profile from said sensor output signals;
   extracting one or more values describing said first electrical profile;
   comparing said one or more values of said first electrical profile with one or more values of at least one other electrical profile of a known vapor; and
   generating digital encoded information associated with one of said at least one other electrical profile of a known vapor which matches said detected electrical profile.

5. The method as claim in claim 4, wherein said electrical profile is a voltage profile.

6. The method as claimed in claim 1, wherein said sensor array comprises a plurality of groupings of one or more sensors, each grouping configured to detect a different vapor.

7. The method as claimed in claim 1, wherein said sensor array comprises a plurality of the same sensor, wherein a different filter is associated with each sensor of said plurality of the same sensor which differentially affects the passage or flow of different molecules across the filter.

8. The method as claimed in claim 1, further comprising the step of recording one or more bioelectric properties of the olfactory cortex in said subject with at least one recording electrode.

9. The method as claimed in claim 8, wherein said at least one recording electrode is an integral part of said implantable electrode array.

10. The method as claimed in claim 1 wherein said stimulating step stimulates the olfactory bulb.

11. A system for mimicking a sense of smell in a subject, comprising:
a sensor array comprising a plurality of sensors for detecting one or more vapors, said sensor array producing sensor output signals in response to detecting said one or more vapors;
a processor for processing said sensor output signals into digital encoded information;
a transmitter for transmitting said digital encoded information transcutaneously into said subject;
a receiver-stimulator configured to receive said transcutaneously transmitted digital encoded information and generate electrical impulses as a function thereof, wherein said electrical impulses are determined according to training conducted by a user; and
an implantable electrode array comprising at least one stimulating electrode configured to stimulate the olfactory cortex in said subject with said electrical impulses.

12. The system as claimed in claim 11, wherein said electrical impulses are associated with spatio-temporal electrical stimulation patterns.

13. The system as claimed in claim 11, wherein each of said at least one stimulating electrode of said implantable electrode array is individually controllable.

14. The system as claimed in claim 11, wherein said sensor array comprises a plurality of groupings of one or more sensors, each grouping configured to detect a different vapor.

15. The system as claimed in claim 11, wherein said sensor array comprises a plurality of the same sensor, wherein a different filter is associated with each sensor of said plurality of the same sensor which differentially affects the passage or flow of different molecules across the filter.

16. The system as claimed in claim 11, further comprising at least one recording electrode for recording one or more bioelectric properties of the olfactory cortex in said subject.

17. The system as claimed in claim 16, wherein said at least one recording electrode is an integral part of said implantable electrode array.

18. The system as claimed in claim 11 wherein the implantable electrode array is configured for stimulating the olfactory bulb.

* * * * *